US012655464B2

(12) United States Patent
Yamashita et al.

(10) Patent No.: US 12,655,464 B2
(45) Date of Patent: Jun. 16, 2026

(54) ELECTROPHORETIC COLLECTION DEVICE AND NUCLEIC ACID PRETREATMENT DEVICE

(71) Applicant: Hitachi High-Tech Corporation, Tokyo (JP)

(72) Inventors: Eri Yamashita, Tokyo (JP); Yukio Ono, Tokyo (JP); Mima Ogawa, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 677 days.

(21) Appl. No.: 18/025,157

(22) PCT Filed: Sep. 24, 2020

(86) PCT No.: PCT/JP2020/035978
§ 371 (c)(1),
(2) Date: Mar. 7, 2023

(87) PCT Pub. No.: WO2022/064587
PCT Pub. Date: Mar. 31, 2022

(65) Prior Publication Data
US 2023/0313267 A1     Oct. 5, 2023

(51) Int. Cl.
*C12Q 1/6806* (2018.01)
(52) U.S. Cl.
CPC ................................. *C12Q 1/6806* (2013.01)
(58) Field of Classification Search
None
See application file for complete search history.

(56) References Cited

U.S. PATENT DOCUMENTS 4,954,237 A * 9/1990 Sarrine ............ G01N 27/44782
204/616
5,384,022 A * 1/1995 Rajasekaran .... G01N 27/44717
204/620

(Continued)

FOREIGN PATENT DOCUMENTS

JP      2002-502020 A      1/2002
JP      2004-144532 A      5/2004

(Continued)

OTHER PUBLICATIONS

International Search Report (PCT/ISA/210) issued in PCT Application No. PCT/JP2020/035978 dated Oct. 27, 2020 with English translation (four (4) pages).

(Continued)

*Primary Examiner* — J. Christopher Ball
(74) *Attorney, Agent, or Firm* — Crowell & Moring LLP

(57)     ABSTRACT

Preprocessing samples for nucleic acid analysis requires a means for effectively and accurately size-fractionating and dividing a nucleic acid sample in order to remove foreign substances that will negatively impact analysis performance. The present invention provides an electrophoretic collection device characterized by comprising: a collection hole for collection of a nucleic acid sample that has undergone electrophoretic separation; a light source 6 that radiates excitation light onto the nucleic acid sample; a detector 7 that detects light that has been emitted from the sample due to the radiated light; and a dispensing mechanism 9, 10, 11 that collects a nucleic acid sample solution within the collection hole, wherein the light source, detector, and dispensing mechanism can access the collection hole from respectively different directions.

8 Claims, 8 Drawing Sheets

(56)    References Cited

U.S. PATENT DOCUMENTS

| | | | |
|---|---|---|---|
| 6,146,511 A | 11/2000 | Slater et al. | |
| 6,793,790 B1 * | 9/2004 | Olivares .......... | G01N 27/44717 204/461 |
| 2004/0079639 A1 | 4/2004 | Adachi et al. | |

FOREIGN PATENT DOCUMENTS

| | | | | |
|---|---|---|---|---|
| JP | 2004-170362 A | 6/2004 | | |
| JP | 2004-290109 A | 10/2004 | | |
| WO | WO-2014098761 A1 * | 6/2014 | ....... | G01N 27/44726 |
| WO | WO 2017/159084 A1 | 9/2017 | | |

OTHER PUBLICATIONS

Japanese-language Written Opinion (PCT/ISA/237) issued in PCT Application No. PCT/JP2020/035978 dated Oct. 27, 2020 (three (3) pages).

* cited by examiner

[FIG. 1]
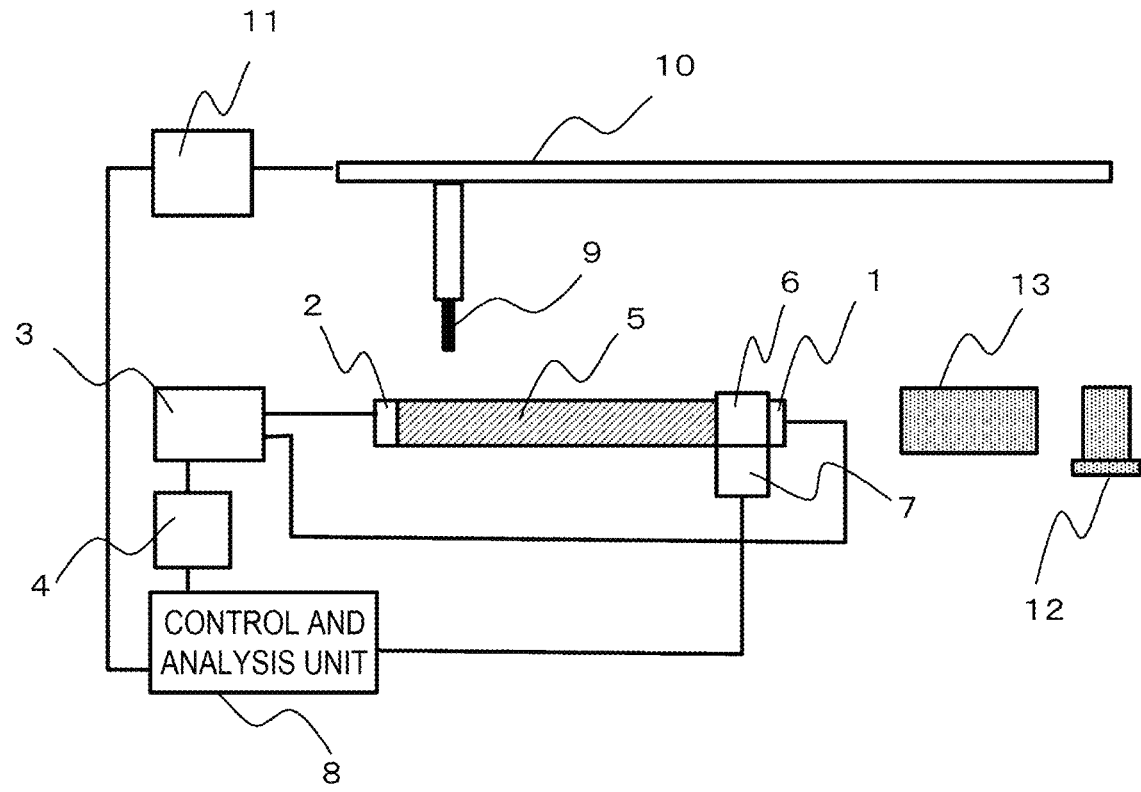
[FIG. 2]
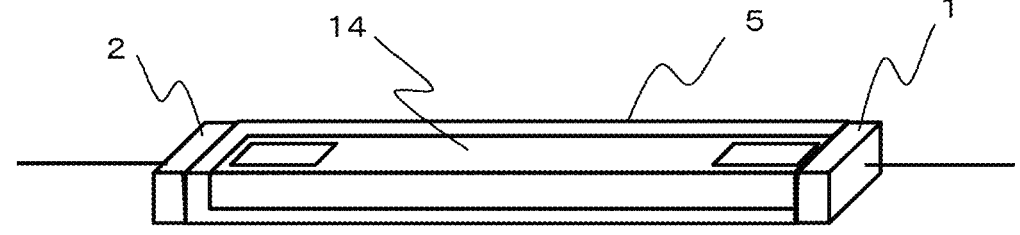

[FIG. 3]
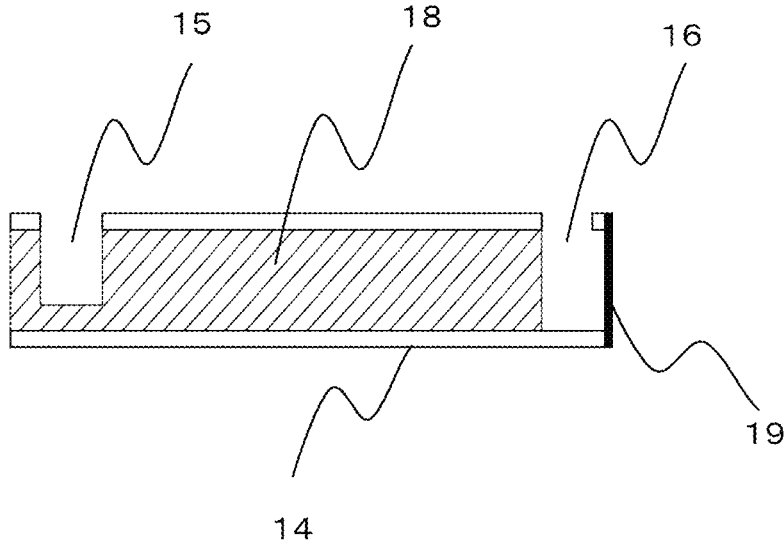
[FIG. 4]
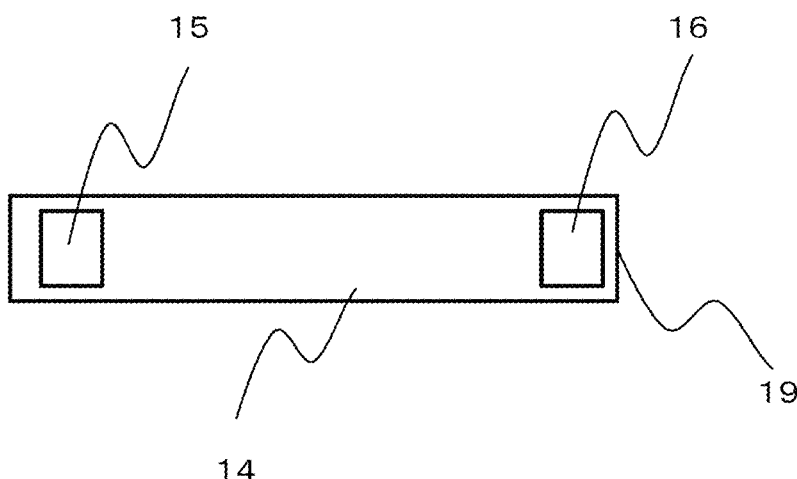
(VIEW VIEWED FROM ABOVE)

[FIG. 5]
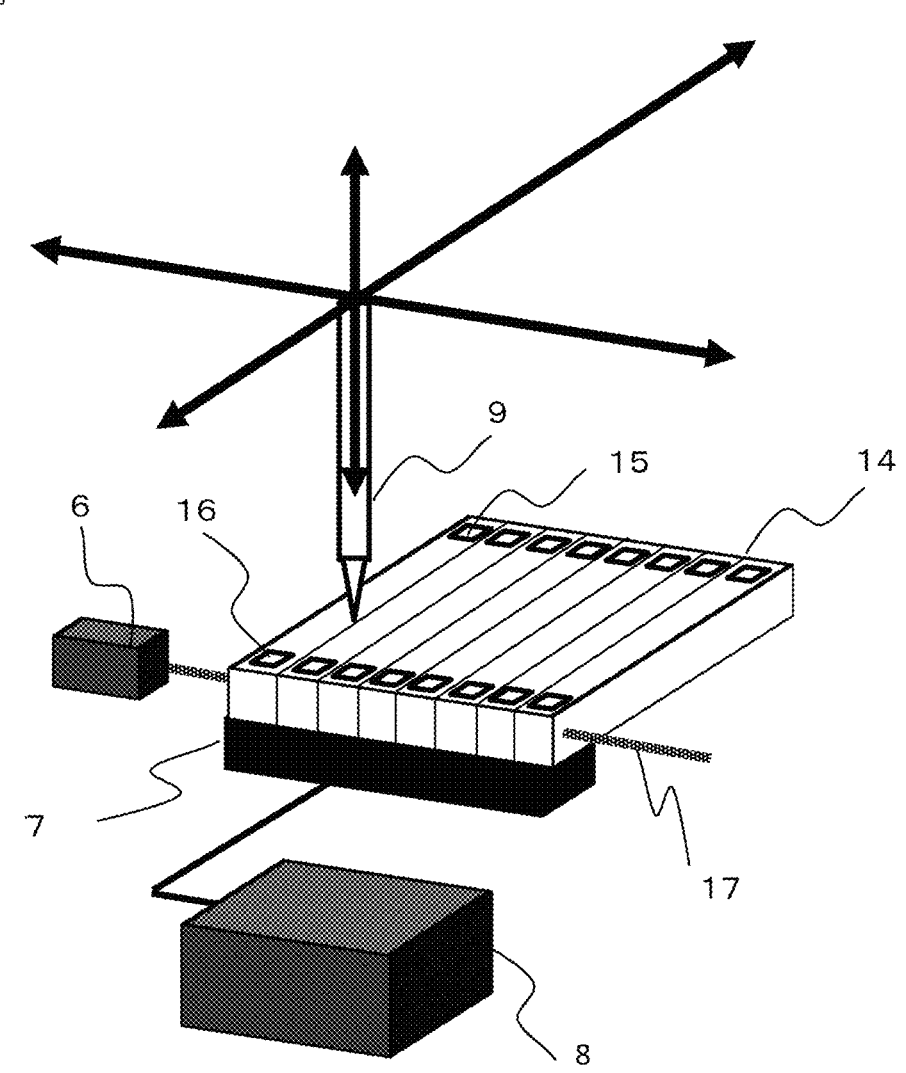

[FIG. 6]
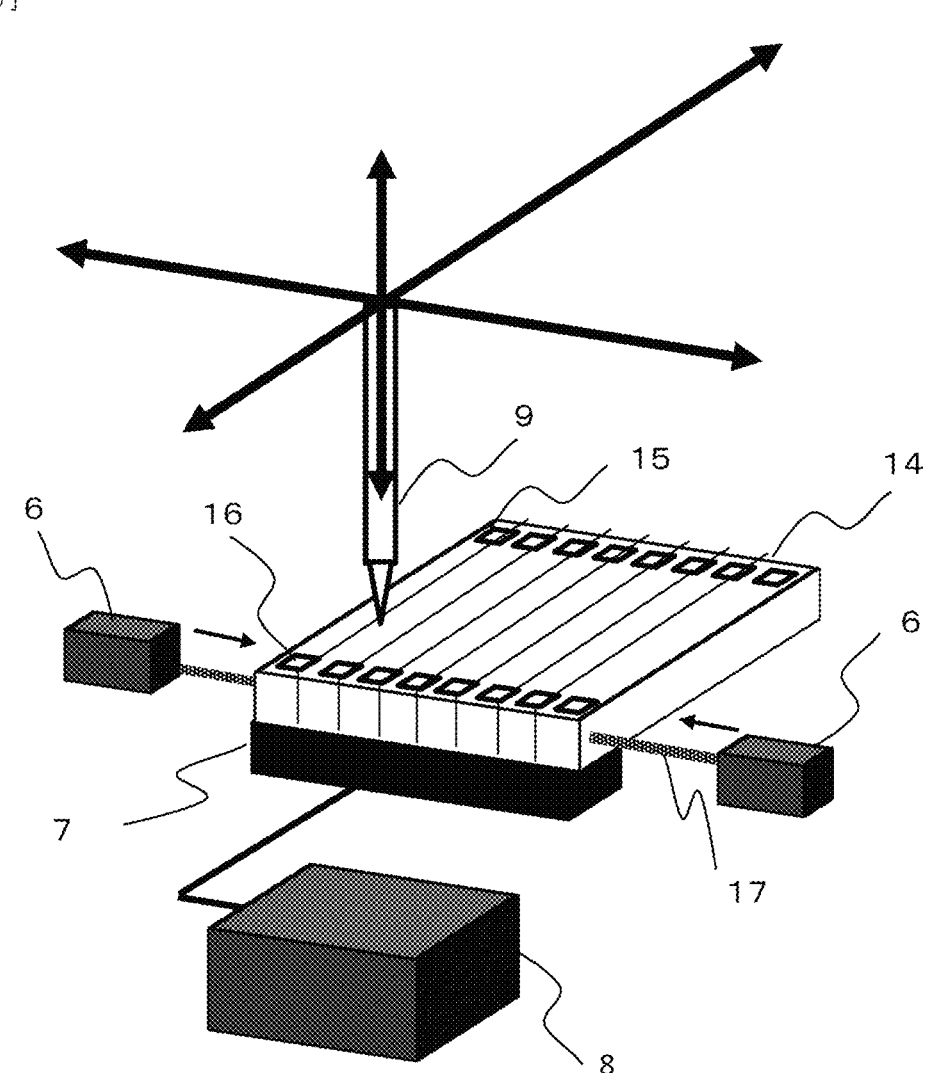

[FIG. 7]
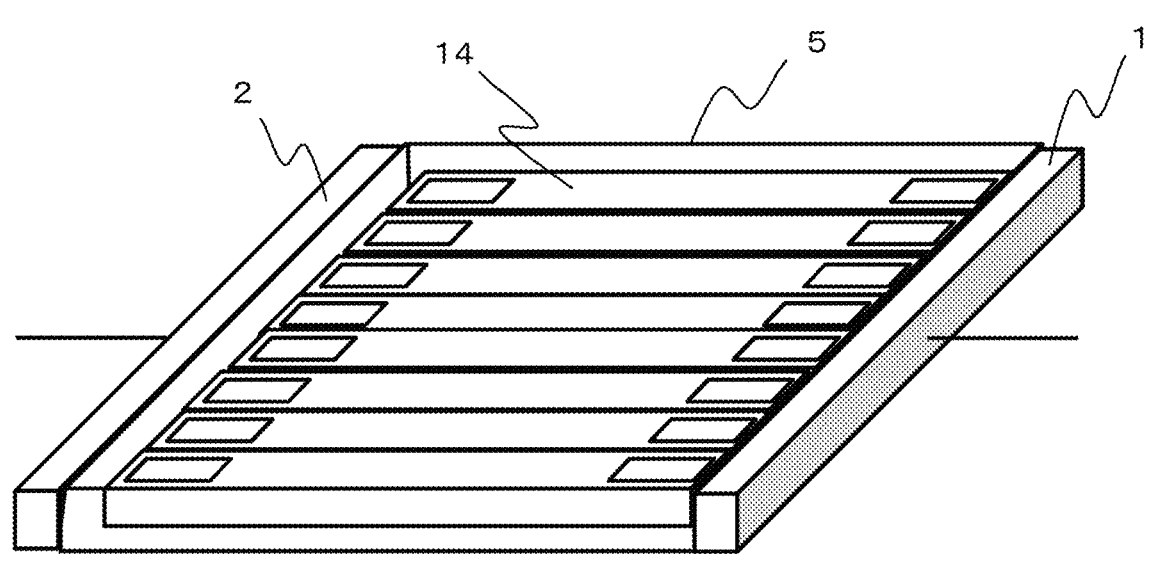

[FIG. 8]
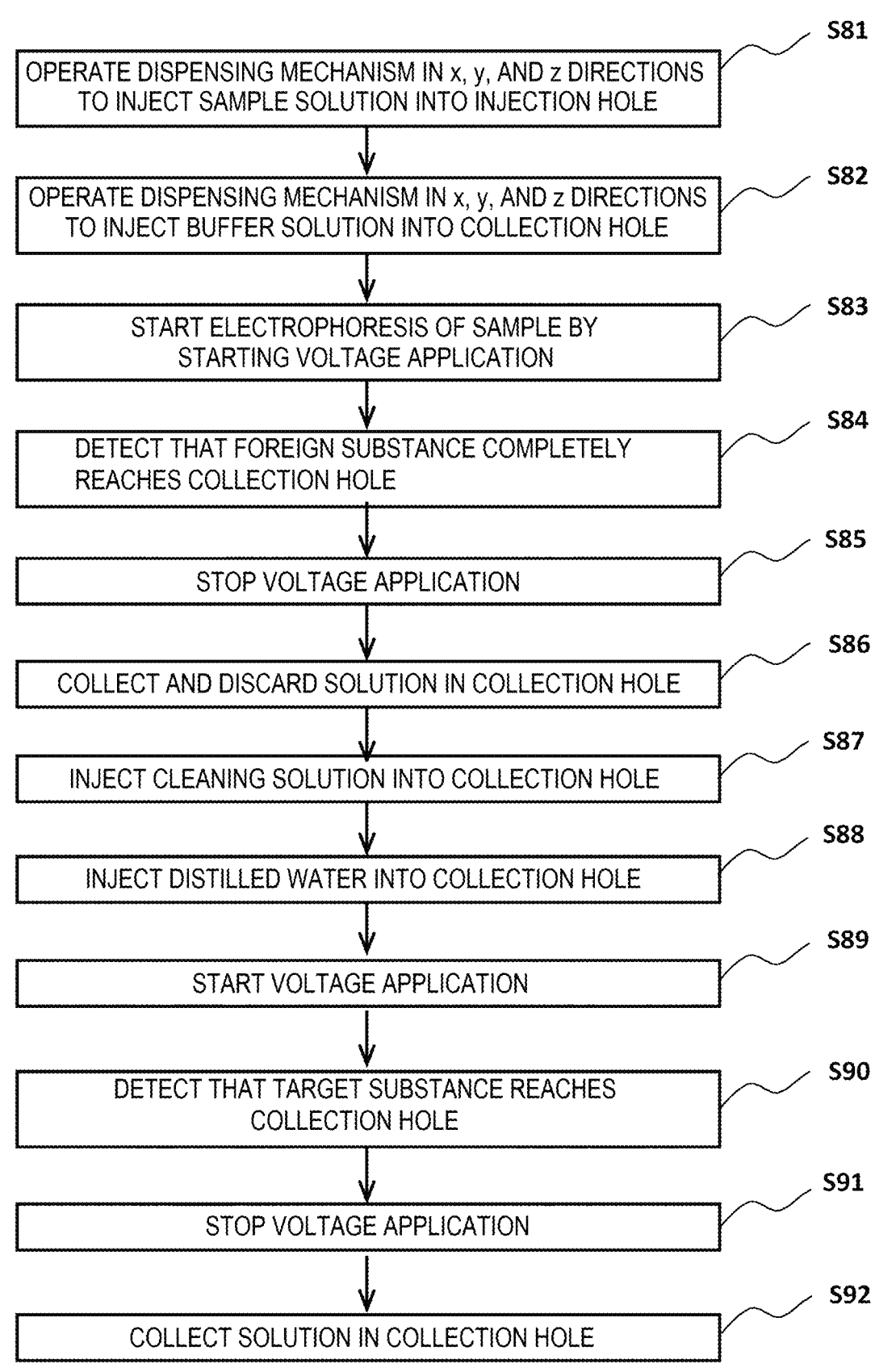

[FIG. 9]
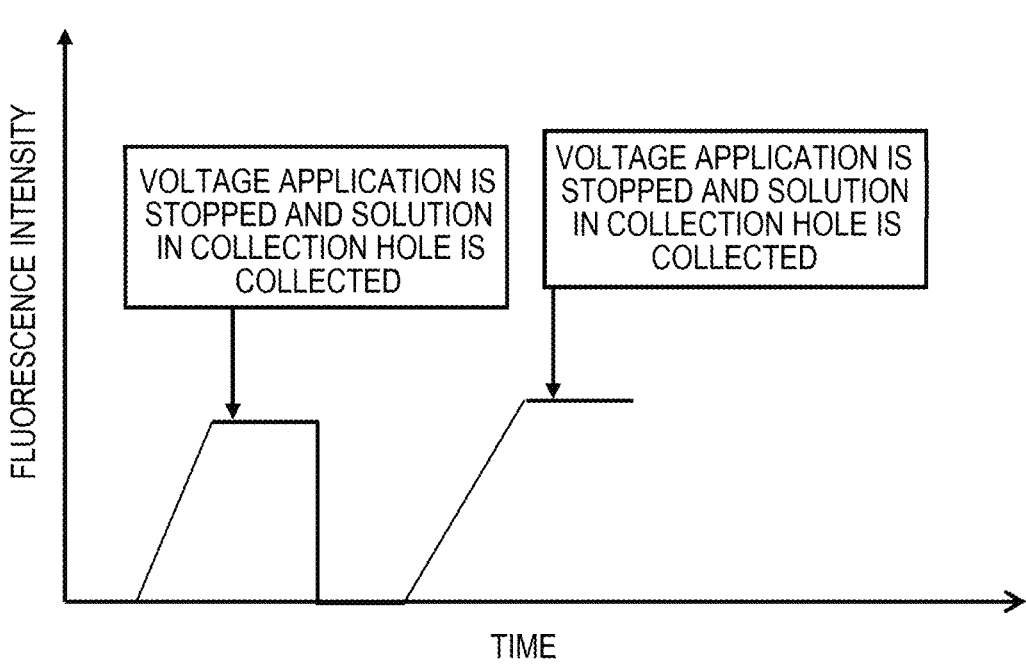

[FIG. 10]
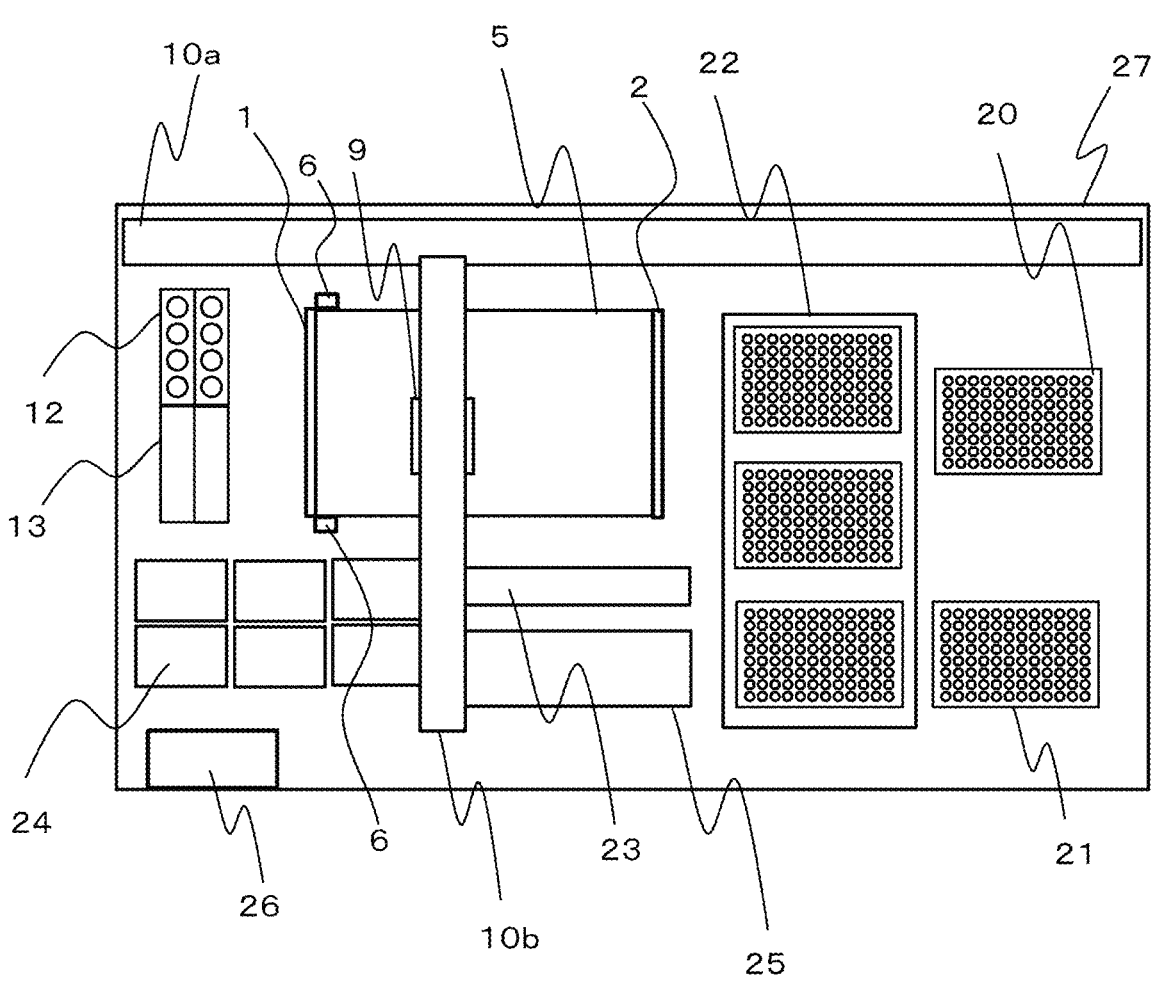

ELECTROPHORETIC COLLECTION DEVICE AND NUCLEIC ACID PRETREATMENT DEVICE

TECHNICAL FIELD

The present invention relates to a nucleic acid collection technique for purifying and collecting a nucleic acid by electrophoresis.

BACKGROUND ART

In an analysis of various biological samples, a demand for analyzing nucleic acids such as DNA and RNA, for example, genetic diagnosis and a gene analysis, has been increasing in recent years. A sample pretreatment when analyzing a nucleic acid includes a step of size-fractionating and purifying a nucleic acid sample. A method using a magnetic bead or a spin column is used for separation and purification of the nucleic acid. The same method using the magnetic bead or the spin column may be used depending on a size of the nucleic acid to be fractionated, but in some cases, the method cannot be used depending on the sample to be fractionated. Therefore, in many cases, an electropho-resis method is generally used in a size fractionation that requires more accuracy. Electrophoresis mainly includes capillary electrophoresis and gel electrophoresis.

For example, PTL 1 discloses fractionation and dividing of a biological substance using the capillary electrophoresis. In the dividing using the gel electrophoresis, a method for excising and collecting a target band separated by the electrophoresis together with each gel is generally used. PTL 2 discloses a method for providing a collection hole in a gel instead of excising the gel, allowing a DNA having a small size to pass through the collection hole, visually checking that a DNA having a target size is separated by the electrophoresis, and collecting the DNA having the target size, and a method for dividing, by a filter, and collecting a biological substance reaching the collection hole without monitoring the separation by the electrophoresis.

CITATION LIST

Patent Literature

PTL 1: JP2004-144532A
PTL 2: JP2004-290109A

SUMMARY OF INVENTION

Technical Problem

In various nucleic acid analyses, for example, in a base sequence analysis using a next-generation DNA sequencer, one pretreatment step for a sample to be subjected to a sequence analysis is preparation of a DNA library. In general, the preparation of the DNA library is a step of ampli-fying and fragmenting a DNA extracted from a cell or blood serving as a sample, adding adapter sequences to both ends of the DNA to amplify and purify the DNA, and obtaining the DNA library. At this time, a target substance is obtained by adding the adapters to both ends of the DNA fragment. However, at the same time, DNA sequences each having a size smaller than that of the target substance, such as a DNA fragment having an adapter sequence added only to one end and a dimer of the adapter sequence, are generated as foreign substances. When these foreign substances are not removed and sequencing is performed, an opportunity to sequence a sequence of the target substance is deprived, and an amount of obtained data is reduced. This also relates to success or failure of the analysis. Therefore, it is desirable to remove these foreign substances before the sequencing, and a method for easily and accurately size-fractionating and dividing the nucleic acid sample is required. A treatment volume of the nucleic acid sample to be pretreated may be large, and it is also desired that a large amount of nucleic acids can be separated by a single treatment.

The electrophoresis method is widely known for the size fractionation of a sample in the related art. In particular, in terms of an ability to treat a biological sample at one treatment, it is generally possible to treat more samples in the electrophoresis method using the gel as compared with the capillary electrophoresis. However, when the size frac-tionation using the gel electrophoresis is performed, an excision method in the related art includes a step of excising a target site from the gel after the electrophoresis and extracting the sample, and a problem arises that the method requires skill and takes time. In the method in PTL 2 described above, in a case in which a fractionation size of the foreign substance and a fractionation size of the target substance are close to each other, the accuracy of separation and dividing is deteriorated, and the method may not be able to cope with the case. When many foreign substances are present, the fractionation size of the target substance may be mixed depending on a time during which the foreign sub-stances pass through the collection hole.

Therefore, an object of the invention is to provide a nucleic acid collection device and a nucleic acid pretreat-ment device using gel electrophoresis, which solve these problems.

Solution to Problem

In the invention, in order to achieve the above object, an example of a nucleic acid collection device according to the invention is an electrophoretic collection device for purify-ing a nucleic acid sample. The electrophoretic collection device includes: electrodes configured to perform electro-phoresis of the nucleic acid sample; a voltage application unit configured to apply a voltage to the electrodes; an electrophoresis tank; a light source configured to emit exci-tation light onto the nucleic acid sample separated by the electrophoresis; a detector configured to detect excited light; a control and analysis unit configured to monitor and quan-tify the detected light; and a dispensing mechanism config-ured to collect the nucleic acid sample separated by the electrophoresis. An electrophoresis gel provided in the elec-trophoresis tank includes an injection hole through which the nucleic acid sample is injected and a collection hole through which the nucleic acid sample fractionated by the electrophoresis is collected. The light source is provided such that the collection hole is irradiated transversely from a side surface of the collection hole with the emitted excitation light.

In order to achieve the above object, a nucleic acid pretreatment device for purifying a nucleic acid sample includes: a temperature control unit; a magnetic plate unit; a reaction plate; and an electrophoretic collection device. The electrophoretic collection device includes electrodes configured to perform electrophoresis of the nucleic acid sample, a voltage application unit configured to apply a voltage to the electrodes, an electrophoresis tank, a light source configured to emit excitation light onto the nucleic acid sample separated by the electrophoresis, a detector configured to detect excited light, a control and analysis unit configured to monitor and quantify the detected light, and a dispensing mechanism configured to collect the nucleic acid sample separated by the electrophoresis. An electrophoresis gel provided in the electrophoresis tank includes an injection hole through which the nucleic acid sample is injected and a collection hole through which the nucleic acid sample fractionated by the electrophoresis is collected. The light source is provided such that the collection hole is irradiated transversely from a side surface of the collection hole with the excitation light emitted from the light source.

Advantageous Effects of Invention

According to the nucleic acid collection device of the invention, it is possible to easily divide, with a high purification degree, a nucleic acid sample having a target size distribution from a nucleic acid sample in which a foreign substance remains.

BRIEF DESCRIPTION OF DRAWINGS

FIG. 1 is a schematic side view of a nucleic acid collection device according to a first embodiment.

FIG. 2 is an installation diagram of an electrophoresis tank for a gel mold according to the first embodiment.

FIG. 3 is a vertical cross-sectional view of the gel mold according to the first embodiment.

FIG. 4 is a plan view of the gel mold according to the first embodiment.

FIG. 5 is a schematic perspective view of an installation of a plurality of gel molds according to the first embodiment.

FIG. 6 is a schematic perspective view of two light sources in the installation of the plurality of gel molds according to the first embodiment.

FIG. 7 is an installation diagram in which the plurality of gel molds are provided in the electrophoresis tank according to the first embodiment.

FIG. 8 is a workflow diagram showing a workflow for collecting a nucleic acid sample according to the first embodiment.

FIG. 9 is a graph showing a correlation between a detected fluorescence intensity and an electrophoresis time according to the first embodiment.

FIG. 10 is a plan view of an overall configuration of a nucleic acid pretreatment device according to a second embodiment.

DESCRIPTION OF EMBODIMENTS

Hereinafter, embodiments of the invention will be described with reference to the drawings.

First Embodiment

The present embodiment is an embodiment of an electrophoretic collection device and a nucleic acid pretreatment device. The electrophoretic collection device includes: electrodes configured to perform electrophoresis of a nucleic acid sample; a voltage application unit configured to apply a voltage to the electrodes; an electrophoresis tank; a light source configured to emit excitation light onto the nucleic acid sample separated by the electrophoresis; a detector configured to detect excited light; a control and analysis unit configured to monitor and quantify the detected light; and a dispensing mechanism configured to collect the nucleic acid sample separated by the electrophoresis. An electrophoresis gel provided in the electrophoresis tank includes an injection hole through which the nucleic acid sample is injected and a collection hole through which the nucleic acid sample fractionated by the electrophoresis is collected. The light source is provided such that the collection hole is irradiated transversely from a side surface of the collection hole with the emitted excitation light.

First, the nucleic acid sample that needs to be treated by the nucleic acid collection device will be described. For example, a DNA library is used as a sample that is to be subjected to an analysis requiring a pretreatment of a nucleic acid, such as a sequence analysis. The DNA library used for the sequence analysis is prepared by different methods depending on methods for performing the sequence analysis. Enzymes used for preparation of the DNA library are commercially available from various reagent manufacturers. Therefore, a detailed procedure and the like depend on a protocol of each reagent. Description of details will be omitted, and an outline will be described.

First, an outline of a method for preparing the DNA library prior to size fractionation, which is one of pretreatment steps of the sample to be subjected to the sequence analysis, will be described.

First, a nucleic acid sample extracted from a biological sample such as a cell, blood, and a formalin-fixed paraffin embedded tissue is fragmented. A method using an ultrasonic wave is used in the fragmentation of the nucleic acid sample, but a procedure of a method using an enzyme is shown here as an example. The nucleic acid sample extracted from the biological sample is dispensed into a tube together with a reaction reagent such as an enzyme, and is incubated and fragmented at a reaction temperature. The reaction temperature and a reaction time vary depending on the reagent to be used. After a lapse of a predetermined reaction time, the fragmentation reaction is stopped. It is necessary to add an adapter sequence to the fragmented nucleic acid sample in order to provide the nucleic acid sample on a primer sequence, an analysis substrate, or the like for the sequence analysis, and thus a terminal modification of the nucleic acid sample is performed. For example, an enzyme treatment for smoothing a terminal of the nucleic acid sample or adding an overhanging nucleotide is performed. A reaction solution containing an enzyme and the like is added to the tube containing the fragmented nucleic acid sample and is incubated for a predetermined time. The terminal modification may not be performed when a target terminal is modified by the fragmentation of the nucleic acid sample. After completion of the terminal treatment reaction, the adapter sequence is added. The adapter sequence varies depending on the analysis method. The adapter sequence and the reaction solution such as an enzyme are added to the tube and are incubated to prepare the DNA library. Usually, a DNA library for purification is prepared by amplifying the prepared DNA library by the adapter sequence. The solution replacement and purification for each reaction are performed by a method using magnetic beads or ethanol precipitation.

Next, an example of preparation of the electrophoresis gel used for the size fractionation of the DNA library will be described. Various types of electrophoresis gels are used, and an agarose gel and a polyacrylamide gel are often used. The size fractionation using the gel has a separation degree varying depending on a concentration of agarose or acrylamide, which is a component of the gel, and is used according to a purpose. An example of preparation of a polyacrylamide gel will be described with reference to FIGS. 3 and 4.

FIG. 3 is a vertical sectional view of a gel mold. FIG. 4 is a plan view of the gel mold as viewed from above. The polyacrylamide gel having an injection hole 15 and a collection hole 16 is prepared. A gel mold 14 shown in FIG. 3 includes the injection hole 15 and the collection hole 16. Since a plurality of gel molds 14 may be arranged in parallel during the electrophoresis, it is preferable to use an insulating and heat-resistant material. In addition, since an excitation light from a light source or light such as fluorescence passes through at least collection portions on a side surface and a bottom surface, it is preferable to use a material having a high transmittance. Examples thereof include various materials such as PS, PMMA, glass, and quartz. For the gel mold 14, for example, a gel solution containing a 40% acrylamide/bis solution (19:1) is poured into the gel mold 14. The injection hole 15 and the collection hole 16 are each molded by inserting a comb before the gel solution is solidified. After the gel solution is solidified, the comb is removed, and a membrane 19 is added to the side surface on a collection hole side. The membrane 19 is preferably a semipermeable membrane or the like through which the nucleic acid sample cannot pass.

The gel mold 14 described above has a structure in which both electrode sides have no insulating material and have a part or the entirety of the surface open, and both side surfaces different from the both electrode sides are surrounded by the insulating material. As a different example, a structure in which the both side surfaces are open may be used. In this case, the gel solution is similarly poured and molded after a film or the like is attached to block the openings.

Subsequently, the nucleic acid collection device according to the present embodiment will be described with reference to FIGS. 1, 2, 5, 6, and 7.

FIG. 1 is a schematic view showing the nucleic acid collection device. FIG. 2 is an installation diagram of an electrophoresis tank for a gel mold. FIG. 5 is a schematic perspective view of an installation of a plurality of gel molds. FIG. 6 is a schematic perspective view of two light sources in the installation of the plurality of gel molds. FIG. 7 is an installation diagram in which the plurality of gel molds are provided in the electrophoresis tank.

As shown in FIG. 1, the nucleic acid collection device according to the invention includes: a positive electrode 1 and a negative electrode 2 that are used to perform the electrophoresis of the nucleic acid sample; a voltage application device 3 that applies a voltage to the electrodes; a voltage control unit 4 that controls the applied voltage; an electrophoresis tank 5; a light source 6 that emits, from a side surface of the electrophoresis tank, an excitation light onto the nucleic acid sample separated by the electrophoresis; and a detector 7 that detects excited light and is provided on a bottom surface of the electrophoresis tank 5. A reason why the light source 6 is arranged on the side surface and the detector 7 is arranged on the bottom surface is that the light source 6 and the detector 7 are arranged effectively for easy access since a dispensing probe 9 accesses from an upper surface of the electrophoresis gel.

The nucleic acid collection device further includes a sample and reagent holder 12 that holds the nucleic acid sample and the reagent and a buffer tank 13 that holds a buffer solution, distilled water, and the like. The nucleic acid collection device also includes a dispensing mechanism that injects the nucleic acid sample into the electrophoresis gel and collects the separated nucleic acid sample. The dispensing mechanism includes the dispensing probe 9, a dispensing mechanism driving unit 10, and a dispensing mechanism control unit 11. The positive electrode 1 and the negative electrode 2 are in contact with the buffer solution in the electrophoresis tank 5. A control and analysis unit 8 can monitor the detected light, perform an analysis, and calculate an amount based on the detected light. The control and analysis unit 8 can also control the dispensing mechanism, control the injection of the nucleic acid sample into the injection hole, the dispensing of the solution into the collection hole, the collection, cleaning, and control the electrophoresis to control start and stop of the electrophoresis.

FIG. 2 is a diagram showing the arrangement of the electrophoresis layer tank 5 and the gel mold 14 in a simplified manner. As shown in FIG. 2, the gel mold 14 containing a polyacrylamide gel is horizontally provided in an electrophoresis device. At this time, the light source 6 is provided such that the collection hole 16 is irradiated transversely from a side surface of the collection hole 16 with excitation light 17 emitted from the light source 6. At least one electrophoresis gel is irradiated transversely, but when a plurality of electrophoretic gels are arranged, a plurality of gel molds 14 are arranged as shown in FIG. 5, and a position of the light source may be on an opposite side. As shown in FIG. 6, two light sources may be provided such that collection holes 16 are irradiated transversely from both side surfaces of the collection holes 16. In particular, when the plurality of gel molds are provided, the excited light can be stably detected in the case in which the excitation light is emitted from the light sources on both sides as compared with the case in which the excitation light is emitted from the light source on one side. In FIGS. 5 and 6, the gel molds 14 are arranged side by side, and a positional relation among the light source, the gel molds 14, and the detector 7 is shown in a simplified manner. The arrangement of the electrophoresis tank 5, the electrode 1, and the electrode 2 is as shown in FIGS. 2 and 7. When the plurality of gel molds 14 are arranged side by side, it is possible to prevent mixing of other samples by using the gel molds 14 each having a structure surrounded by the insulating material on both side surfaces different from both electrode sides.

The detector 7 may be a photodiode or a two-dimensional sensor such as a CCD camera or a CMOS. When the detector 7 is a photodiode, it is preferable to provide at least one photodiode for each of the gel molds 14 such that the light can be detected from each of the gel molds 14. When the detector 7 is a two-dimensional sensor such as a CCD camera or a CMOS, one or more sensors may be used for the plurality of gel molds 14 such that the light can be detected from all collection holes of the plurality of gel molds 14. In this case, the light detected according to a region of each collection hole is analyzed. When the detector 7 is a photodiode, depending on a size of the photodiode, a detectable size of the gel mold 14 is approximately fixed according to a detection range. However, when the detector 7 is a two-dimensional sensor such as a CCD camera or a CMOS, the detector 7 can cope with the situation by setting a detection region even when sizes of the gel molds 14 are different. Therefore, there is an advantage that a variation in gel size is increased.

The buffer solution, for example, a 1×TBE buffer solution (Tris Borate EDTA Buffer) is charged into the electrophoresis tank 5. The buffer solution fills the gel mold 14 up to an edge of an upper surface thereof. The TBE buffer solution is also charged into the injection hole 15 and the collection hole 16. Volumes of the buffer solution charged into the collection hole 16 and the buffer solution filling a periphery of the gel mold 14 are set such that the buffer solutions do not mix with each other. Although the TBE buffer solution is used as an example of the buffer solution, another buffer solution for the electrophoresis may be used.

FIG. 8 is a flowchart of dispensing a sample into the injection hole 15 by the dispensing mechanism, size-fractionating the sample by the electrophoresis, and collecting a nucleic acid sample, i.e., a target substance, and includes steps S81 to S92 as shown in the same figure.

That is, a nucleic acid sample that is mixed with a fluorescent dye or the like for nucleic acid detection and is to be subjected to the size fractionation is set in the sample and reagent holder 12 in FIG. 1, and the sample is dispensed into the injection hole 15 by the dispensing mechanism. The dispensing probe 9 is moved to the coordinates of a sample solution placed in the sample and reagent holder 12 by the dispensing mechanism driving unit 10, is moved again to the coordinates of the injection hole 15 by the dispensing mechanism after suctioning the sample solution, and dispenses the nucleic acid sample into the injection hole 15.

After dispensing the sample, a voltage of 100 V is applied to start the electrophoresis. By applying the voltage, the sample in the injection hole 15 is subjected to electrophoresis toward the collection hole 16, and the nucleic acid sample is size-fractionated. The nucleic acid sample contains foreign substances and a target substance. When the nucleic acid sample is prepared by the nucleic acid sample preparation method described above, the target substance is one obtained by adding adapters to both ends of a DNA fragment. The foreign substances to be mainly removed include DNA sequences each having a size smaller than that of the target substance, such as a DNA fragment having an adapter sequence added only to one end and a dimer of the adapter sequence. When the size is smaller than that of the target substance, an electrophoresis speed is high. When the collection hole 16 is irradiated with the excitation light 17 from the light source 6 and the sample reaches the collection hole 16, the detector 7 detects fluorescence emitted from the sample.

FIG. 9 is a diagram showing a correlation between a fluorescence intensity detected by the detector and an electrophoresis time. First, the foreign substance having a small size and a high electrophoresis speed reaches the collection hole 16, and the fluorescence intensity starts to increase. When a time elapses and at a time point at which an increase rate of the fluorescence intensity is reduced, it is detected that the foreign substance completely reaches the collection hole, and the voltage application is stopped. The detection that the foreign substance completely reaches is based on a premise that the foreign substance and the target substance can be separated by the gel electrophoresis. The time point at which the increase rate of the fluorescence intensity is reduced and the voltage application is stopped indicates that a gradient of the increase in the fluorescence intensity decreases, but the fluorescence intensity may decrease depending on an electrophoresis condition. Therefore, a timing at which the voltage application is stopped includes a period from the time when the foreign substance reaches the collection hole to the time when the increase in the fluorescence intensity starts due to reaching of the target substance to the collection hole. In order to reduce mixing of the foreign substance, the voltage application may be stopped at a timing at which the target substance starts to reach the collection hole and the increase in the fluorescence intensity starts again.

A foreign substance solution in the collection hole 16 is suctioned and collected by the dispensing probe 9 and is removed. When a plurality of size-fractionated foreign substances are present in front of the target substance, the foreign substances may be collectively removed. Alternatively, the foreign substances may be removed one by one. When the foreign substances are to be removed one by one, the buffer solution is injected into the collection hole 16 by the probe 9 after collecting and removing the foreign substances. The foreign substance and the target substance may be distinguished from each other by, for example, estimating in advance the time point at which the target substance reaches the collection hole 16 and elapsing the time. It is also possible to specify the number of the timings at which the fluorescence intensity increases and the voltage is stopped based on an electrophoresis image confirmed by the electrophoresis in advance, and to distinguish the target substance from the foreign substance. Since the target substance may be different depending on a user, it is possible for a person skilled in the art to appropriately set and automatically collect the target substance.

After the foreign substance is discarded, the collection hole 16 is cleaned by a cleaning solution before the electrophoresis for collecting the target substance is started. The buffer solution, the distilled water, or the like contained in the buffer tank 13 is used as the cleaning solution. The cleaning is performed by injecting and discarding the cleaning solution into and from the collection hole 16 by the probe 9. The cleaning may be performed a plurality of times. Accordingly, it is possible to reduce a risk of the mixing of the foreign substance.

After the collection hole 16 is cleaned, the distilled water contained in the buffer tank 13 is injected into the collection hole 16 by the probe 9 as a solvent for collecting the target substance, and the voltage application is restarted. The solvent for collecting the target substance may be changed to a buffer solution depending on an intended use of the target substance. The target substance reaches the collection hole 16, and the fluorescence intensity starts to increase. When a time elapses and at a time point at which the increase rate of the fluorescence intensity is reduced, the voltage application is stopped. The time point at which the increase rate of the fluorescence intensity is reduced and the voltage application is stopped indicates that the gradient of the increase in the fluorescence intensity decreases in the graph of the fluorescence intensity and the time in FIG. 9, but the fluorescence intensity may decrease depending on the electrophoresis condition. In general, the collection at a point at which the gradient of the increase in the graph of the fluorescence intensity and the time becomes zero is optimal in consideration of a purification degree and a collection amount. Although this depends on the DNA sample, in some cases, the target substance can be obtained with a purification degree of 95% or more in the case of collecting the target substance with emphasis on the purification degree.

The target substance in the collection hole 16 is collected by the dispensing mechanism and is divided into the sample and reagent holder 12 provided for collection. A volume of the solvent for collecting the target substance depends on the gel size, and it is sufficient that the volume enables the electrophoresis and collection of the target substance. An amount and a concentration of the collected target substance can be calculated based on the volume of the solvent for collecting and the fluorescence intensity detected in the collection hole 16. The obtained target substance solution can be divided and adjusted according to a purpose of a subsequent use. Since the amount and the concentration of the target substance contained in the collected target substance solution are clarified, when the next operation is performed using the target substance solution, dispensing can be performed in an appropriate amount, and troubles such as a detection error during a final sequence analysis can be avoided.

According to the present embodiment described above, it is possible to prevent a loss of the nucleic acid sample in which an amount of DNA is limited, and to obtain a result having higher reliability.

Second Embodiment

An example of a nucleic acid pretreatment device of the second embodiment will be described with reference to FIG. 10. The nucleic acid pretreatment device according to the present embodiment is capable of preparing the DNA library and the like, which is one of the pretreatment steps, and further includes the configuration of the nucleic acid collection device shown in the first embodiment, which is capable of size-fractionating a nucleic acid sample such as an prepared DNA library, removing the foreign substance, and dividing the target nucleic acid sample.

A nucleic acid pretreatment device 27 includes: the positive electrode 1 and the negative electrode 2 that are used to perform electrophoresis of the nucleic acid sample; the electrophoresis tank 5; the light sources 6 that emit excitation light onto the nucleic acid sample separated by the electrophoresis; a detector that detects excited light; the dispensing probe 9; an X-axis dispensing mechanism driving unit 10*a*; a Y-axis dispensing mechanism driving unit 10*b*; the sample and reagent holder 12 that holds the nucleic acid sample and a reagent; the buffer tank 13 that holds a buffer solution or distilled water; a temperature control unit 20; a magnetic plate unit 21; a reaction plate 22; a waste liquid tank 23; a pipette tip rack 24; a disposal pipette tip box 25; and a control and analysis unit 26 that can register the sample, control and instruct operations within the device, monitor and analyze the detected light, calculate an amount based on the detected light, and store the amount.

For example, a sample that is to be subjected to an analysis requiring a pretreatment of a nucleic acid sample, such as a sequence analysis is provided. A method for preparing the DNA library, which is one of pretreatment steps of the sample to be subjected to the sequence analysis, is shown. DNA extraction from a biological sample such as a cell or blood requires various operations depending on the biological sample to be extracted, and thus description thereof will be omitted in the present embodiment, and an extracted DNA sample is used for description.

The DNA library used for the sequence analysis is prepared by different methods depending on a method for performing the sequence analysis. Enzymes used for preparation of the DNA library are commercially available from various reagent manufacturers. Therefore, description regarding a name of the enzyme, a detailed procedure, and the like is omitted because the above details depend on a protocol of each reagent.

First, the DNA sample extracted from blood, saliva, a cell, a formalin-fixed paraffin embedded tissue or the like is fragmented. A method using an ultrasonic wave is used in the fragmentation of the DNA sample, but a procedure of a method using an enzyme is shown here as an example.

The DNA sample extracted from the biological sample and a reaction reagent such as an enzyme for the fragmentation are provided in the sample and reagent holder 12, dispensed into a reaction tube together, and incubated by the temperature control unit 20. A reaction temperature and a reaction time vary depending on the reagent to be used. After a lapse of a predetermined reaction time, the fragmentation reaction is stopped. When the fragmentation reaction is stopped, a method for stopping the reaction varies, such as addition of a stop reagent depending on the fragmentation reagent used and thermal denaturation of the enzyme by overheating. When the reaction solution is replaced after the fragmentation, magnetic beads are added to the fragmented DNA sample solution, and adsorption is performed by a magnetic force in the magnetic plate unit 21 to perform purification. In the following operation, when it is necessary to replace the solution, the magnetic beads are added to perform the purification in the same manner.

Next, terminal modification of the DNA sample is performed. When the terminal is not sufficient for adding an adapter for the sequence analysis, an enzyme treatment for smoothing a terminal of the nucleic acid sample or adding an overhanging nucleotide is performed in the terminal modification. The terminal modification is not performed when the fragmentation treatment of the DNA sample results in a terminal shape to which the adapter for the sequence analysis can be added. In the terminal modification, a reaction solution containing an enzyme, a base, and the like for the terminal modification is added to the fragmented DNA sample, and is incubated by the temperature control unit 20 for a predetermined time.

After completion of the terminal modification reaction, the adapter is added. The adapter sequence varies depending on the analysis method. An adapter sequence solution and a reaction solution such as an enzyme provided in the sample and reagent holder 12 are added to the reaction tube and are incubated by the temperature control unit 20. After the adapter addition reaction, the magnetic beads are added to the DNA sample, and adsorption is performed by the magnetic force in the magnetic plate unit 21 to perform the purification. The DNA library to be subjected to the size fractionation is prepared by adding a reagent, a primer, or the like for nucleic acid amplification after the DNA sample is purified, performing PCR by the temperature control unit 20, amplifying the DNA sample, and purifying the reaction solution.

Next, the size fractionation of the DNA library is performed. An electrophoresis gel used for the size fractionation is the same as the electrophoresis gel in the first embodiment, and thus description of a method for preparing the electrophoresis gel is omitted. The size fractionation of the DNA library and collection of a target substance solution are performed in the same method as in the first embodiment. The size-fractionated and collected target substance solution is obtained in a specified tube in the sample and reagent holder 12. An amount and a concentration of the collected target substance can be calculated based on a volume of a solvent for collecting and a fluorescence intensity detected in the collection hole 16. The obtained target substance solution can be divided and adjusted according to a purpose of a subsequent use.

In the present embodiment, a plurality of DNA samples can be treated at the same time. When a plurality of DNA samples extracted from the biological sample are provided and cannot be charged into the sample and reagent holder 12, the plurality of DNA samples extracted from the biological sample can be provided on the reaction plate 22 to cope with the situation. The size-fractionated and collected target substance solution can also be obtained by the reaction plate 22 in the same manner.

When a wide variety of DNA samples are subjected to the same analysis, by changing the adapter sequences added according to the DNA samples, even different DNA libraries can be mixed and treated in the case of performing the size fractionation. Accordingly, it is possible to shorten a treatment time.

The invention is not limited to the embodiments described above and includes various modifications. For example, the embodiments described above have been described in detail for better understanding of the invention, and the invention is not necessarily limited to those including all configurations described above.

Further, although an example of creating a program for implementing a part or all of the configurations, functions, and the control and analysis unit described above is mainly described, it is needless to say that a part or all of them may be implemented by hardware, for example, by designing an integrated circuit. That is, all or a part of functions of a processing unit may be implemented by, for example, an integrated circuit such as an application specific integrated circuit (ASIC) or a field programmable gate array (FPGA) instead of the program.

REFERENCE SIGNS LIST

1: positive electrode
2: negative electrode
3: voltage application device
4: voltage control unit
5: electrophoresis tank
6: light source
7: detector
8, 26: control and analysis unit
9: dispensing probe
10: dispensing mechanism driving unit
10a: dispensing mechanism driving unit (X-axis)
10b: dispensing mechanism driving unit (Y-axis)
11: dispensing mechanism control unit
12: sample and reagent holder
13: buffer tank
14: gel mold
15: injection hole
16: collection hole
17: excitation light
18: gel (separation medium)
19: membrane
20: temperature control unit
21: magnetic plate unit
22: reaction tube plate
23: waste liquid tank
24: pipette tip rack
25: disposal pipette tip box
26: control and analysis unit
27: nucleic acid pretreatment device

The invention claimed is:

1. An electrophoretic collection device for purifying a nucleic acid sample, the electrophoretic collection device comprising:
electrodes configured to perform electrophoresis of the nucleic acid sample;
a voltage application unit configured to apply a voltage to the electrodes;
an electrophoresis tank;
a light source configured to emit excitation light onto the nucleic acid sample separated by the electrophoresis;
a detector configured to detect excited light;
a control and analysis unit configured to monitor and quantify the detected light; and
a dispensing mechanism configured to collect the nucleic acid sample separated by the electrophoresis, wherein

12 an electrophoresis gel provided in the electrophoresis tank includes an injection hole through which the nucleic acid sample is injected and a collection hole through which the nucleic acid sample fractionated by the electrophoresis is collected,
the light source is provided such that the collection hole is irradiated transversely from a side surface of the collection hole with the emitted excitation light,
the detector is provided such that the excited light is detected from a bottom surface of the collection hole, and
the light source configured to emit the light onto the collection hole transversely from the side surface of the collection hole includes light sources configured to emit light onto the collection hole transversely from both sides.

2. The electrophoretic collection device according to claim 1, wherein
for the nucleic acid sample fractionated by the electrophoresis, the excitation light for the nucleic acid sample excited in the collection hole is detected, and the separated and fractionated nucleic acid sample is quantified, and
the separated and fractionated nucleic acid sample is collected by the dispensing mechanism.

3. The electrophoretic collection device according to claim 1, wherein
by an increase rate of an intensity of the light excited by the excitation light emitted from the light source, setting of solution collection from the collection hole is performed and the solution is collectable automatically.

4. The electrophoretic collection device according to claim 1, wherein
a plurality of gel molds for the electrophoresis are used to separate and fractionate the corresponding nucleic acid samples, and detection and quantification of the nucleic acid samples reaching the collection hole are simultaneously performed for the nucleic acid samples in the respective gel molds.

5. A nucleic acid pretreatment device for purifying a nucleic acid sample, the nucleic acid pretreatment device comprising:
a temperature control unit;
a magnetic plate unit;
a reaction plate; and
an electrophoretic collection device, wherein
the electrophoretic collection device includes electrodes configured to perform electrophoresis of the nucleic acid sample, a voltage application unit configured to apply a voltage to the electrodes, an electrophoresis tank, a light source configured to emit excitation light onto the nucleic acid sample separated by the electrophoresis, a detector configured to detect excited light, a control and analysis unit configured to monitor and quantify the detected light, and a dispensing mechanism configured to collect the nucleic acid sample separated by the electrophoresis, wherein
an electrophoresis gel provided in the electrophoresis tank includes an injection hole through which the nucleic acid sample is injected and a collection hole through which the nucleic acid sample fractionated by the electrophoresis is collected, and
the light source is provided such that the collection hole is irradiated transversely from a side surface of the collection hole with the excitation light emitted from the light source, the detector is provided such that the excited light is detected from a bottom surface of the collection hole, and the light source configured to emit the light onto the collection hole transversely from the side surface of the collection hole includes light sources configured to emit light onto the collection hole transversely from both sides.

6. The nucleic acid pretreatment device according to claim 5, wherein for the nucleic acid sample fractionated by the electrophoresis, the excitation light for the nucleic acid sample excited in the collection hole is detected, the separated and fractionated nucleic acid sample is quantified, and the separated and fractionated nucleic acid sample is collected by the dispensing mechanism.

7. The nucleic acid pretreatment device according to claim 5, wherein by an increase rate of an intensity of the light excited by the excitation light emitted from the light source, setting of solution collection from the collection hole is performed and the solution is collectable automatically.

8. The nucleic acid pretreatment device according to claim 5, wherein a plurality of gel molds for the electrophoresis are used to separate and fractionate the corresponding nucleic acid samples, and detection and quantification of the nucleic acid samples reaching the collection hole are simultaneously performed for the nucleic acid samples in the respective gel molds.

* * * * *